US010121182B1

(12) United States Patent
Wood et al.

(10) Patent No.: US 10,121,182 B1
(45) Date of Patent: Nov. 6, 2018

(54) GENERATING MEDIA RECOMMENDATIONS BASED UPON BEATS PER MINUTE

(71) Applicant: Amazon Technologies, Inc., Reno, NV (US)

(72) Inventors: James H. Wood, Seattle, WA (US); Patrick C. Teo, San Carlos, CA (US); Benjamin L. Shepherd, Issaquah, WA (US); Korwin J. Smith, Seattle, WA (US); Scott Durham, Seattle, WA (US); Piragash Velummylum, Seattle, WA (US); Emily J. Butler, San Francisco, CA (US)

(73) Assignee: Amazon Technologies, Inc., Seattle, WA (US)

( * ) Notice: Subject to any disclaimer, the term of this patent is extended or adjusted under 35 U.S.C. 154(b) by 927 days.

(21) Appl. No.: 14/138,381

(22) Filed: Dec. 23, 2013

Related U.S. Application Data (62) Division of application No. 13/222,761, filed on Aug. 31, 2011, now Pat. No. 8,626,607.

(51) Int. Cl.
*G06Q 30/00* (2012.01)
*G06Q 30/06* (2012.01)

(52) U.S. Cl.
CPC ..... *G06Q 30/0631* (2013.01); *G06Q 30/0625* (2013.01); *G06Q 30/0641* (2013.01)

(58) Field of Classification Search
CPC ........... G06Q 30/06; G06Q 30/0601–30/0643; G06Q 30/08; G06Q 2220/00; G06Q 2220/10; G06Q 2220/12; G06Q 2220/123; G06Q 2220/127; G06Q 2220/14; G06Q 2220/145; G06Q 2220/16; G06Q 2220/165; G06Q 2220/18
See application file for complete search history.

(56) References Cited

U.S. PATENT DOCUMENTS

| | | |
|---|---|---|
| 2002/0181711 A1 | 12/2002 | Logan et al. |
| 2006/0080335 A1 | 4/2006 | Freeborg et al. |
| 2008/0065469 A1 | 3/2008 | Specter et al. |
| 2008/0103689 A1 | 5/2008 | Graham et al. |
| 2008/0281895 A1* | 11/2008 | McKinney ........ G06F 17/30743 708/424 |

(Continued)

OTHER PUBLICATIONS www.mongomusic.com; Oct. 18, 2000, (Oct. 18, 2000).

(Continued)

*Primary Examiner* — William J Allen
(74) *Attorney, Agent, or Firm* — Thomas | Horstemeyer, LLP (57) ABSTRACT

Disclosed are various embodiments relating to generating media item recommendations based upon determining a beats per minute value. A media recommendation application determines a beats per minute value based upon the activity of a user. The media recommendation application then identifies one or more media item candidates having a number of beats per minute within a predefined delta of the beats per minute value. The media recommendation application then filters out the media items possessed and information associated with the user to identify a subset of the media item candidates to surface as recommendations.

19 Claims, 8 Drawing Sheets

(56) References Cited

U.S. PATENT DOCUMENTS

| | | | |
|---|---|---|---|
| 2010/0169340 A1* | 7/2010 | Kenedy | G06Q 30/0631 707/758 |
| 2010/0273610 A1* | 10/2010 | Johnson | A63B 24/0075 482/9 |
| 2010/0282045 A1 | 11/2010 | Chen et al. | |
| 2010/0287071 A1* | 11/2010 | Shah | G06Q 10/10 705/26.25 |
| 2011/0154198 A1* | 6/2011 | Bachman | G06F 17/30026 715/704 |
| 2012/0030230 A1 | 2/2012 | Sheinkop et al. | |
| 2012/0158531 A1* | 6/2012 | Dion | G06Q 10/10 705/26.1 |
| 2012/0323737 A1 | 12/2012 | Pousti et al. | |
| 2012/0331386 A1 | 12/2012 | Hicken et al. | |

OTHER PUBLICATIONS

Stone, Brad, Hitting the right notes, Newsweek Jul. 3, 2000, 64,66, vol. 135, 1.

Levack, Kinley, Tracking Down Tracks: Search Engine Evolve, EContent 27. 4 (Apr. 2004): 7-9.

U.S. Appl. No. 13/222,779, filed Aug. 31, 2011, Examiner's Answer to Appeal Brief dated Sep. 9, 2016.

U.S. Appl. No. 13/222,779, filed Aug. 31, 2011, Advisory Action dated Oct. 28, 2015.

U.S. Appl. No. 13/222,779, filed Aug. 31, 2011, Response to Final Office Action dated Jul. 2, 2015.

U.S. Appl. No. 13/222,779, filed Aug. 31, 2011, Final Office Action dated Jul. 2, 2015.

U.S. Appl. No. 13/222,779, filed Aug. 31, 2011, Response to Non-Final Office Action dated Dec. 22, 2014.

U.S. Appl. No. 13/222,779, filed Aug. 31, 2011, Non-Final Office Action dated Dec. 22, 2014.

U.S. Appl. No. 13/222,779, filed Aug. 31, 2011, Response to Final Office Action dated Feb. 22, 2013.

U.S. Appl. No. 13/222,779, filed Aug. 31, 2011, Final Office Action dated Feb. 22, 2013.

U.S. Appl. No. 13/222,779, filed Aug. 31, 2011, Response to Non-Final Office Action dated Sep. 13, 2012.

U.S. Appl. No. 13/222,779, filed Aug. 31, 2011, Non-Final Office Action dated Sep. 13, 2012.

U.S. Appl. No. 13/222,761, filed Aug. 31, 2011, Notice of Allowance dated Sep. 5, 2013.

U.S. Appl. No. 13/222,761, filed Aug. 31, 2011, Response to Non-Final Office Action dated Apr. 29, 2013.

U.S. Appl. No. 13/222,761, filed Aug. 31, 2011, Non-Final Office Action dated Apr. 29, 2013.

U.S. Appl. No. 13/222,761, filed Aug. 31, 2011, Response to Restriction/Election dated Mar. 12, 2011.

U.S. Appl. No. 13/222,761, filed Aug. 31, 2011, Restriction/Election dated Mar. 12, 2013.

\* cited by examiner

GENERATING MEDIA RECOMMENDATIONS BASED UPON BEATS PER MINUTE

CROSS REFERENCE TO RELATED APPLICATIONS/INCORPORATION BY REFERENCE

This application is a divisional of U.S. application Ser. No. 13/222,761 titled "Generating Media Recommendations Based Upon Beats Per Minute," filed Aug. 31, 2011, which is incorporated herein by reference in its entirety.

BACKGROUND

People searching media items online usually enter search terms according to their music preferences. For example, a user may search according to a specific genre of music, such as, jazz or classic rock.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

DETAILED DESCRIPTION

Various embodiments of the present disclosure relate to searching media items based upon a number of beats per minute. In one embodiment, search results that are presented to a user include media items matching the search query along with one or more beats per minute taxonomy concepts, where each of the beats per minute taxonomy concepts comprise a number of beats per minute or a range of beats per minute. The user may then select one of the beats per minute taxonomy concepts in order to identify a portion of the media items associated with the selected beats per minute taxonomy concept. The embodiments disclosed herein also relate to generating recommendations for media items based upon a beats per minute value and information associated with a user account as described herein. In the following discussion, a general description of the system and its components are provided, followed by a discussion of the operation of the same.

Figure 1:
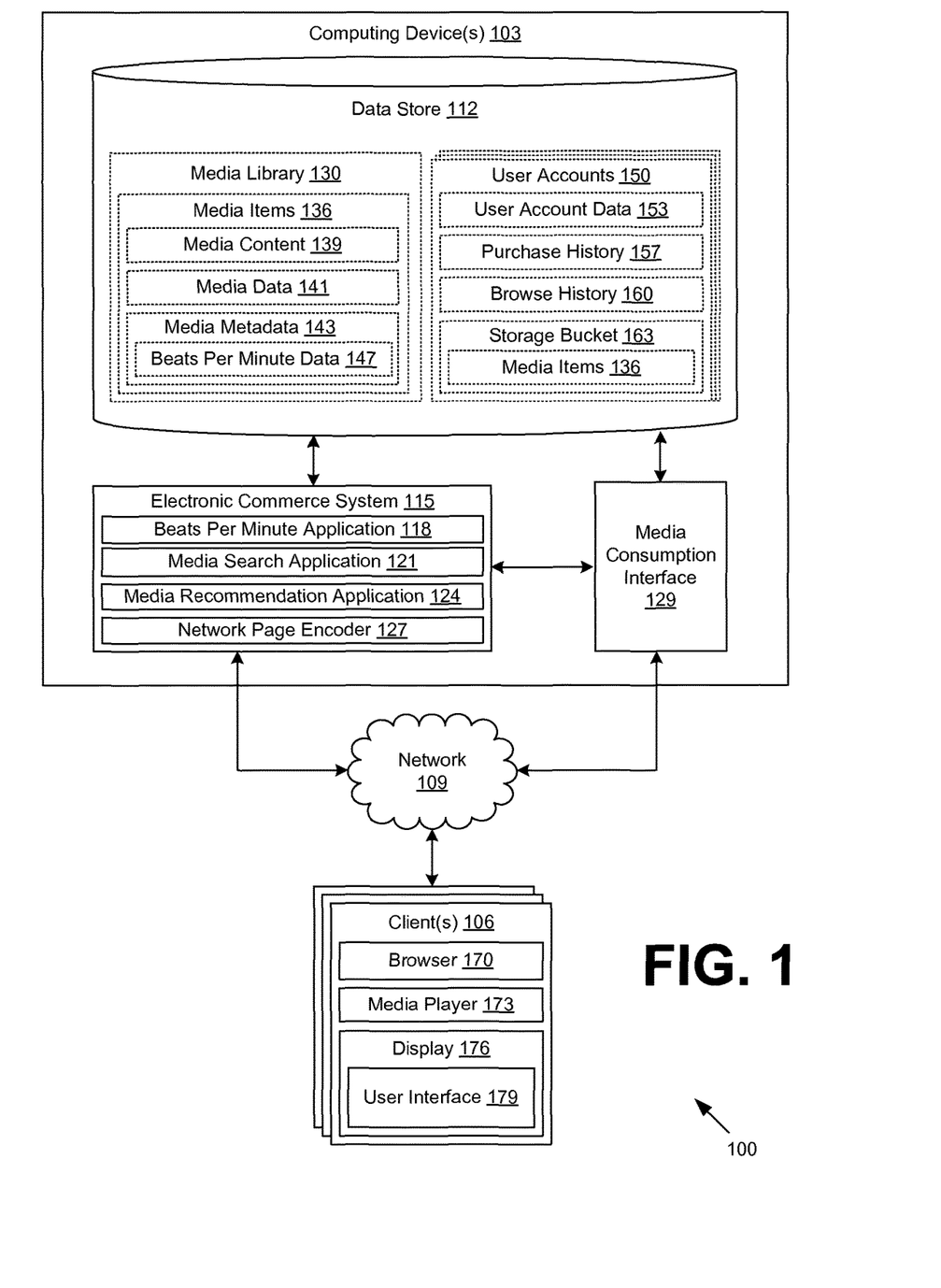
FIG. 1 is a drawing of networked environment according to various embodiments of the present disclosure.

With reference to FIG. 1, shown is a networked environment 100 according to various embodiments. The networked environment 100 includes a computing device 103, clients 106, and a network 109. The network 109 includes, for example, the Internet, intranets, extranets, wide area networks (WANs), local area networks (LANs), wired networks, wireless networks, or other suitable networks, etc., or any combination of two or more such networks.

The computing device 103 may comprise, for example, a server computer or any other system providing computing capability. Alternatively, a plurality of computing devices 103 may be employed that are arranged, for example, in one or more server banks or computer banks or other arrangements. For example, a plurality of computing devices 103 together may comprise a cloud computing resource, a grid computing resource, and/or any other distributed computing arrangement. Such computing devices 103 may be located in a single installation or may be distributed among many different geographical locations. For purposes of convenience, the computing device 103 is referred to herein in the singular. Even though the computing device is referred to in the singular, it is understood that a plurality of computing devices 103 may be employed in the various arrangements as described above.

Various applications and/or other functionality may be executed in the computing device 103 according to various embodiments. Also, various data is stored in a data store 112 that is accessible to the computing device 103. The data store 112 may be representative of a plurality of data stores as can be appreciated. The data stored in the data store 112, for example, is associated with the operation of the various applications and/or functional entities described below.

The components executed on the computing device 103, for example, include an electronic commerce system 115, a media consumption interface 129, and other applications, services, processes, systems, engines, or functionality not discussed in detail herein. The electronic commerce system 115 may include various components, such as, a beats per minute application 118, a media search application 121, a media recommendation application 124, a network page encoder 127, and other applications and/or processes.

The electronic commerce system 115 is executed in order to facilitate the online purchase of media items 136 over the network 109. The electronic commerce system 115 also performs various back-end functions associated with the online presence of a merchant in order to facilitate the online purchase of media items 136. For example, the electronic commerce system 115 may generate various network pages, using the network page encoder 127, such as web pages, or other types of network content that are provided to clients 106 for the purposes of selecting media items 136 for purchase, rental, download, lease, or any other forms of consumption as can be appreciated. Alternatively, a mobile application may be executed in a client 106 to generate and render user interfaces using data served up by the computing device 103 and/or other servers. To this end, when rendered, network pages generate a user interface as can be appreciated.

The media consumption interface 129 is executed to serve up media items 136 stored in the data store 112 to clients 106. The media consumption interface 129 may include a commercially available HTTP server such as, for example, Apache® HTTP Server, Apache® Tomcat®, Microsoft® Internet Information Services (IIS), etc. The media consumption interface 129 may generate one or more network pages, such as web pages, to facilitate selection and consumption of media items 136. In various embodiments, the media consumption interface 129 may serve up code that functions as an embedded audio player, video player, image viewer, etc. in order for the user to consume the media items. Multiple media consumption interfaces 129 may be provided for different platforms of clients 106. For example, one media consumption interface 129 may provide an interface for tablet computers, while another media consumption interface 129 may provide an interface for network-enabled televisions. In one embodiment, the media consumption interface 129 may facilitate consumption of media items 136 through various other media channels and/or subscriptions.

The beats per minute application 118 is executed to identify media items 136 that do not have a beats per minute associated therewith. The beats per minute application 118 may then determine a beats per minute value corresponding to each of the identified media items 136, where the beats per minute value is stored in association with each of the media items 136 as will be described. The media search application 121 may be executed to encode, for rendering by the client 106, one or more search result network pages including a pool of media items 136 in response to a search query and one or more beats per minute taxonomy concepts associated with the pool of media items 136. Lastly, the media recommendation application 124 is executed to generate one or more media recommendations to present to the user based at least upon a determined beats per minute value and information associated with a user account as described herein.

The data stored in the data store 112 includes, for example, a media library 130 of media items 136, user accounts 150, and potentially other data. Associated with each of the media items 136 is media content 139, media data 141, media metadata 143, and potentially other data. The media content 139 comprises, for example, audio content, video content and/or audio/video content associated with each of the media items 136 in the media library 130. The media data 141 comprises information about each of the media items 136, such as, for example, customer reviews, customer ratings, statistics generated from server log data that indicate the number of downloads or previews (e.g., only the first minute of the media item was played out) associated with each of the media items 136, and potentially other data. The media metadata 143 includes beats per minute data 147 comprising a number of beats per minute associated with each of the media items 136, where one or more beats per minute may be associated with each of the media items 136 (e.g. corresponding to slow and fast sections of a song). The media metadata 143 may further comprise other data useful in searching media items 136, such as, for example, media titles, artist titles, media images, genre titles, album titles, media descriptions, media prices, media categories, and potentially other data.

Associated with each user account 150 is, for example, user account data 153, a purchase history 157, a browse history 160, a storage bucket 163, and potentially other data. The user account data 153 may include information about the user and their user account 150, such as, for example, name, address, payment instruments, billing information, account settings, passwords, security credentials, file management permissions, storage quotas and limitations, profile or demographic data associated with users, and/or other data. The purchase history 157 may include data related to a history of purchases of media items 136 through the electronic commerce system 115 by the user. The browse history 160 may comprise data that relates to a history of browsing for media items 136 by a user through the electronic commerce system 115, such as, for example, data relating to the previewing of media items 136. Each user account 150 also comprises a storage bucket 163 for the user to store one or more media items 136 either possessed by the user or purchased from the electronic commerce system 115 as will be described.

The client 106 is representative of a plurality of client devices that may be coupled to the network 109. The client 106 may comprise, for example, a processor-based system such as a computer system. Such a computer system may be embodied in the form of a desktop computer, a laptop computer, a personal digital assistant, a cellular telephone, a smartphone, a set-top box, a music player, a web pad, a tablet computer system, a game console, an electronic book reader, or other devices with like capability.

The client 106 may be configured to execute various applications such as a browser 170, a media player 173, and/or other applications. The browser 170 may be executed in a client 106, for example, to access and render network pages, such as web pages, or other network content served up by the computing device 103 and/or other servers. Alternatively, a mobile application may be executed in a client 106 to generate and render user interfaces 179 using data served up by the computing device 103 and/or other servers. To this end, when rendered, network pages generate a user interface 179 as can be appreciated.

The media player 173 is executed to play out media items 136 obtained through the media consumption interface 129 of the computing device 103. The media player 173 may be a stand-alone application, a plug-in for the browser 170, or other code included within a network page served up by the media consumption interface 129. The client 106 may be configured to execute applications beyond the browser 170 and the media player 173, such as, for example, email applications, instant message applications, and/or other applications.

When executed in a client 106, the browser 170 renders network pages on a respective display 176 and may perform other functions. The browser 170 accesses network pages, such as web pages or other types of content from the computing device 103 in order to access the functionality of the search application 121, the recommendation application 124, and other components implemented in the computing device 103 as will be described.

Next, a general description of the operation of the various components of the networked environment 100 is provided. To begin, the beats per minute application 118 may be executed periodically, or in response to some other trigger, to identify one or more media items 136 in the media library 130 for which there are no beats per minute data 147. Upon identifying a media item 136 with no beats per minute data 147, the beats per minute application 118 may determine a beats per minute value for the media item 136, where the beats per minute value is stored in the beats per minute data 147. In one embodiment, the beats per minute data 147 may comprise multiple beats per minute values for the media item 136 (e.g. corresponding to a slow portion and a fast portion of the media item 136). It is understood that the data generation and analysis functions of the beats per minute application 118 may be implemented within the media search application 121 or some other application.

From time to time, a user possessing one or more media items 136 may wish to transfer such media items 136 into their storage bucket 163 in association with their user account 150. Such a transfer may involve the user uploading the media items 136 to the storage bucket 163 by way of the browser 170, the media player 173, or other applications in the client 106. In addition, the user may also purchase media items 136 through the electronic commerce system 115, which may be automatically uploaded and included in the storage bucket 163 in association with their user account 150.

In one embodiment, the beats per minute application 118 may be executed to identify one or more media items 136 in the storage bucket 163 of one or more user accounts 150 that are not associated with a number of beats per minute. The beats per minute application 118 may then analyze each of the media items 136 to determine a number of beats per minute. To this end, a user may purchase media items 136 or upload media items 136 and organize them based on the number of beats per minute.

Additionally, a user may wish to search for media items 136 to purchase based upon a number of beats per minute. To do so, the user may navigate to an appropriate search link in one or more search network pages to generate a search query. The search network pages may comprise a search field to facilitate the input of one or more search terms describing the media items 136, such as, a field to enter a beats per minute value, an artist name, a genre name, an album name, and potentially other data.

As a non-limiting example, a user may input "150" into a beats per minute search field of a search network page. The user may send the search request to the computing device 103 through the network 109 by clicking on an appropriate button or link. Upon receiving the request, the media search application 121 may execute a search of the beats per minute data 147 associated with the media items 136 to identify a set of media items 136 having 150 beats per minute. Upon identifying the set of media items 136, the media search application 121 generates one or more search result network pages that include the set of media items 136. The media search application 121 then sends the search result network pages over the network 109 to the client 106. A browser 170 or other application executing on the client 106 then renders the search result network pages for display to a user.

In other embodiments, a user may wish to search for media items 136 by entering one or more search terms describing the media items 136. For example, if a user is interested in media items 136 recently released by Madonna, then the user may input the search term "Madonna" into a search field entitled "Artist" and the search term "pop" under the search field entitled "Genre". The user may send the search request to the computing device 103 through the network 109 by clicking on an appropriate button or link.

Upon receiving the request, the media search application 121 may execute a search of the media items 136 to identify a pool of media items 136 based upon the search terms inputted by the user. To this end, the media search application 121 may use one or more approaches to identify the pool of media items 136 from the search terms in the search request. For instance, the media search application 121 may generate the pool of media items 136 by identifying associations between the search terms and the media metadata 143 associated with each of the media items 136. To this end, in the example above, the media search application 121 would search media items 136 associated with the "Pop" genre and the artist entitled "Madonna".

Having determined the pool of media items 136, the media search application 121 may then use the beats per minute data 147 associated with the pool of media items 136 to identify one or more beats per minute taxonomy concepts, where each of the beats per minute taxonomy concepts correspond to a number of beats per minute described by a beats per minute designation. In one embodiment, the beats per minute designation may be a number of beats per minute, such as, for example, "150". In another embodiment, the beats per minute designation may be a range of beats per minute, such as, for instance, "140 to 160".

In yet another embodiment, the beats per minute designation may comprise one or more descriptive terms associated with a range of beats per minute, such as, for instance, "Blues-Like BMP". In this example, a user may select the "Blues-Like BMP" in order to identify one or more media items 136 that have a range of beats per minute commonly associated with media items 136 within the Blues music genre.

Upon identifying the beats per minute taxonomy concepts associated with the pool of media items 136, the media search application 121 generates one or more search result network pages that include the pool of media items 136 and the corresponding beats per minute taxonomy concepts associated with the pool of media items 136. The media search application 121 then sends the search result network pages over the network 109 to the client 106. A browser 170 or other application executing on the client 106 then renders the search result network pages for display to a user.

In one embodiment, the beats per minute taxonomy concepts displayed in the search result network pages may be rendered as a set of links to one or more network pages, where each of the linked network pages correspond to subsequent views of the search results comprising a portion of the media items from the pool of media items 136 that are associated with the respective beats per minute taxonomy concept.

As a non-limiting example, assume that the beats per minute designations comprise of ranges of beats per minute, such as, "100 to 120", "120 to 140", "140 to 160", "160 to 180", and so forth. Further assume that the media search application 121 has identified one hundred media items 136 in response to a search request from a user, where twenty of the media items 136 have a number of beats per minute in the range of "120 to 140", forty of the media items 136 have a number of beats per minute in the range of "140 to 160", and forty of the media items 136 have a number of beats per minute of "160 to 180". In this case, the search result network page would comprise a listing of the one hundred media items 136 and links for each of the beats per minute taxonomy concepts entitled "100 to 140", "140 to "160" and "160 to 180". Thus, if the user selects the "160 to 180" beats per minute taxonomy concept, then the user would be directed to a network page comprising the forty media items 136 that are associated with the "160 to 180" beats per minute designation.

In one embodiment, the media search application 121 may use other data associated with the pool of media items 136 to identify one or more other taxonomy concepts. For example, the media search application 121 may generate one or more search result network pages comprising the pool of media items 136 and one or more genre taxonomy concepts associated a portion of the pool of media items 136. In this example, the search result network page would comprise a listing of the pool of media items 136 and a list of genre taxonomy concepts, such as, for example, "Jazz", "Classic Rock", "Country", and potentially other genres.

In another embodiment, the media search application 121 may generate the search result network pages comprising the pool of media items 136 and one or more activity taxonomy concepts associated with the pool of media items 136, where each of the activity taxonomy concepts comprises a description of an exercise and a suggested range of beats per minute. For example, suppose that the suggested beats per minute for a person walking are between 120 and 140, 150 and 170 for running, and 120 and 140 for cycling. To this end, the search result network page may comprise a listing of the pool of media items 136 and one or more activity taxonomy concepts, such as, for example, "Walking", "Running", and "Cycling". In this example, if the user selects the activity concept entitled "Running", then the user would be directed to a network page comprising a portion of the media items 136 that have a number of beats per minute that is between 150 to 170.

Additionally, in some cases a user may not wish to input one or search terms describing one or more media items 136. As mentioned above, the search network page may comprise a taxonomy comprising one or more categories for the user to select in order to narrow a search of media items 136. To do so, a user may select a category from the taxonomy. The user may send a search request to the computing device 103 through the network 109 by clicking on an appropriate button or link. Upon receiving the request, the media search application 121 may generate one or more category network pages listing the media items 136 associated with the category over the network 109 to the client 106. The media search application 121 then sends the category network pages over the network 109 to the client 106. A browser 170 or other application executing on the client 106 then renders the category network pages, or other user interface, for display to a user.

In one embodiment, the category network pages may comprise a group of the media items 136 associated with the selected category, as well as one or more beats per minute taxonomy concepts associated with the group of media items 136 of the respective category. As noted above, each of the beats per minute taxonomy concepts may be rendered as a set of links to one or more additional network pages showing at least a portion of the group of media items 136 associated with the beats per minute taxonomy concept.

In addition to searching media items 136, in various embodiments, one or more media items 136 may be recommended by the media recommendation application 124 when the user is searching, playing or otherwise rendering media items 136 by the media recommendation application 124. In one embodiment, the browser 170, media player 173, or other applications may be configured to send requests to the media recommendation application 124 to generate media items 136 to recommend to the user. Upon receiving the request, the media recommendation application 124 uses one or more approaches to determine a beats per minute value from which to generate one or more recommendations.

In one embodiment, the media recommendation application 124 may determine a beats per minute value from the search terms inputted by the user. For instance, if a user has generated a search query by inputting the search term "150" in the search field entitled "Beats Per Minute", then the media recommendation application 124 would determine that the beats per minute value is 150.

In another embodiment, the media recommendation application 124 may determine the beats per minute value from a reading of an input device, such as, for example, a pedometer, a heart rate monitor, or other similar devices. To this end, the media recommendation application 124 may use the biomechanics and pacing of the user to determine the beats per minute value closest to the pace of the user for purposes of exercise, etc.

In yet another embodiment, the media recommendation application 124 may determine the beats per minute value from a number of beats per minute of a media item the user is listening. For instance, if the user is listening to a media item with 120 beats per minute, then the media recommendation application 124 would determine that the beats per minute value is 120.

In another embodiment, the media recommendation application 124 may determine the beats per minute value by averaging the number of beats per minute of the media items 136 consumed by the user. For instance, suppose the media items 136 in the storage bucket 163 associated with a user account 150 comprises media items 136 with a range of beats per minute between 160 and 180. In this case, the media recommendation application 124 would determine that the beats per minute value as a range between 160 to 180.

In yet another embodiment, the media recommendation application 124 may determine the beats per minute value from the number of beats per minute associated the media items 136 purchased or sampled by the user, or from the number of beats per minute associated with the media items 136 in one or more playlists generated by the user.

Having determined the beats per minute value, the media recommendation application 124 may execute a search of the media items 136 to identify one or more media candidates based upon the beats per minute value. In one embodiment, the media recommendation application 124 may identify media candidates by searching media items 136 with the same beats per minute value. In other embodiments, the media recommendation application 124 may identify media candidates by searching media items 136 with a number of beats per minute within a predefined delta of the beats per minute value. For instance, if the beats per minute value is "120" and the predefined delta is "10", then the media recommendation application 124 would identify the one or more media candidates having a number of beats per minute between "110" and 130".

After identifying the media candidates, the media recommendation application 124 filters out the media items 136 already possessed by the user by, for example, identifying the media items 136 in the storage bucket 163 associated with the user account 150, or examining the purchase history 157 of the user. Upon filtering out the media items 136 possessed by the user from the media candidates, the media recommendation application 124 may then identify a subset of the media candidates that a user is more likely to purchase or consume based upon information associated with the user account, such as, for example, the user account data 153, the purchase history 157, the browse history 160, playlists, and potentially other data. The media recommendation application 124 then sends the subset of the media item candidates to a requesting process, where the browser 170 or other application executing on the client 106 then renders the subset of media candidates as recommendations for display to a user.

As a non-limiting example, suppose the purchase history 157 of the user indicates that the user has primarily purchased rap media items 136 with a range of beats per minute between 160 to 180. In this example, the media recommendation application 124 may identify a subset of the media item 136 that are associated with a range of beats per minute between 160 and 180 and fall within the genre category of rap. To this end, the media recommendation application 124 may use information from the user account 150 to tailor the subset of media candidates to the likes of the user.

Figure 2:
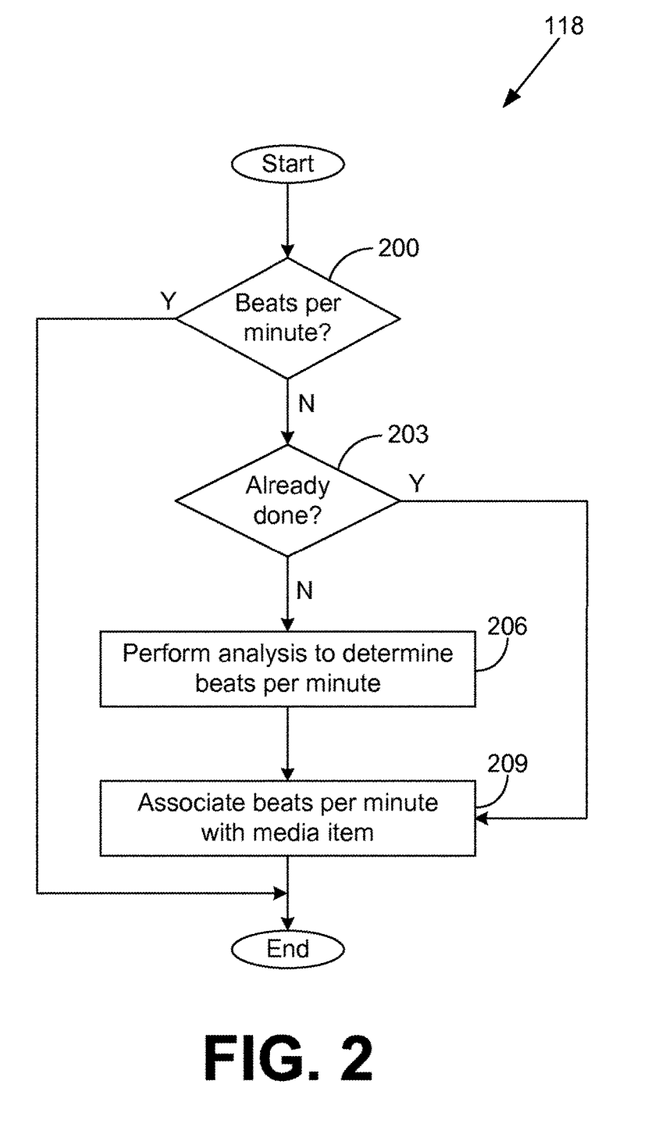
FIG. 2 is a flowchart illustrating one example of functionality implemented as portions of a beats per minute application executed in a computing device in the networked environment of FIG. 1 according to various embodiments of the present disclosure.

Referring next to FIG. 2, shown is a flowchart that provides one example of the operation of a portion of the beats per minute application 118 in generating beats per minute data 147 for media items 136 according to various embodiments. It is understood that the flowchart of FIG. 2 provides merely an example of the many different types of functional arrangements that may be employed to implement the operation of the portion of the beats per minute application 118 as described herein. As an alternative, the flowchart of FIG. 2 may be viewed as depicting an example of steps of a method implemented in the computing device 103 (FIG. 1) according to one or more embodiments.

Beginning with box 200, the beats per minute application 118 may periodically, or upon a purchase or download, determine if a media item 136 has beats per minute data 147 associated therewith. If the media item 136 has beats per minute data 147 associated herewith, then the beats per minute application 118 ends as shown. If the media item 136 does not have beats per minute data 147, then the beats per minute application 118 determines if the media item 136 has already been analyzed in box 203. For example, such may be the case if an earlier instance of the media item 136 had been analyzed on a prior occasion. If the media item 136 has previously been analyzed, then in box 209, the beats per minute application 118 associates the previously determined beats per minute data 147 to the media item 136. If, however, the media item 136 has not been analyzed, then in box 206, the beats per minute application 118 determines a number of beats per minute for the media items 136. Subsequently, in box 209, the beats per minute application 118 associates the number of beats per minute to the analyzed media item 136. The beats per minute application 118 may periodically re-execute steps 200 through 209 as one or more media items 136 are added to the media library 130, or media items 136 are presented in some other way.

Figure 3:
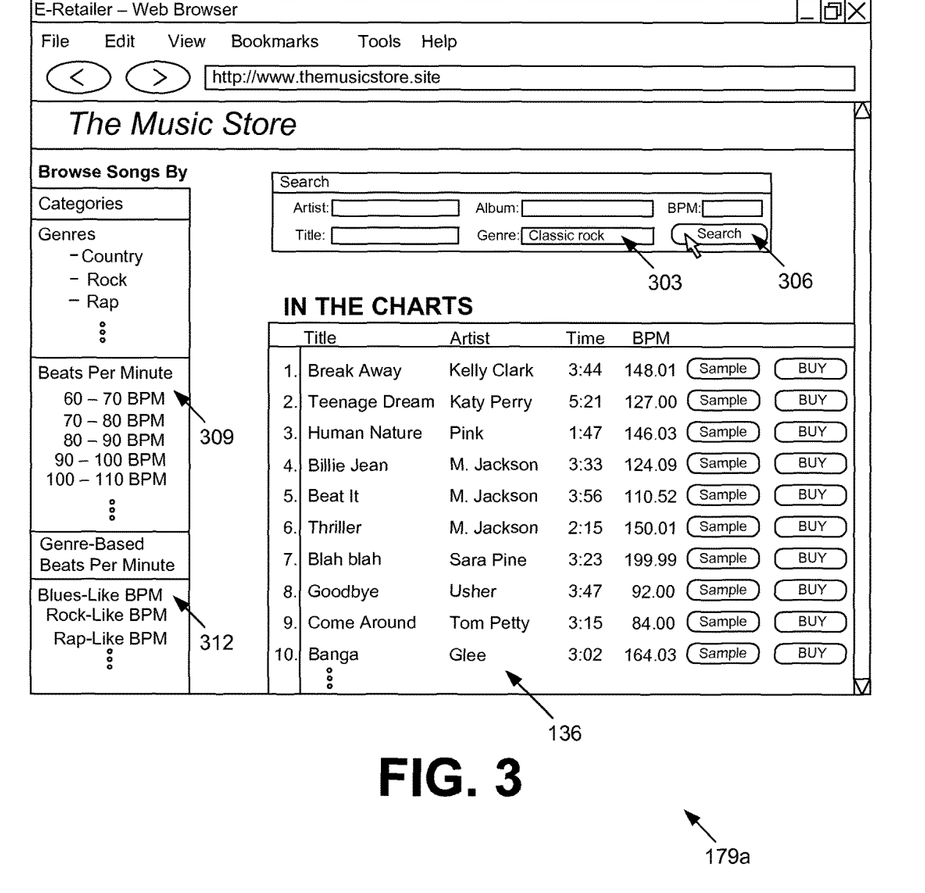
FIG. 3 is a drawing of an example of a user interface rendered by a client in the networked environment of FIG. 1 according to various embodiments of the present disclosure.

Referring next to FIG. 3, shown is a non-limiting example of a user interface 179 (FIG. 1), denoted herein as user interface 179a generated by a media search application 121 (FIG. 1) and rendered by a browser 170 (FIG. 1) executed on a client 106 (FIG. 1).

As a non-limiting example, in FIG. 3, a user has entered the search terms "Classic Rock" within a search query entry field 303 and has executed a search by clicking on a search button 306. It is understood, however, that a search query may be entered in a variety of ways such as, for example, by clicking on a link, by depressing a key on a keyboard, and/or by other methods. As described above, the media search application 121 obtains a search query and generates a pool of media items 136 based at least in part on the search query.

Additionally, user interface 179a comprises the beats per minute taxonomy concepts 309 entitled, "60 to 70", "70 to 80", "80 to 90", "90 to 100", "100 to 110", and so forth. To this end, a user may identify one or more media items 136 associated with a range of beats per minute value by selecting one of the beats per minute taxonomy concepts 309. For instance, the user may select the beats per minute taxonomy concept 309 entitled "100 to 110" to search media items 136 having a range of beats per minute between 100 and 110.

In addition, user interface 179a comprises additional beats per minute taxonomy concepts 312 entitled, "Blues-Like BPM", "Rock-Like BPM", "Rap-Like BPM", and so forth, where each of the additional beats per minute taxonomy concepts 312 is associated with a range of beats per minute or other grouping of beats per minute. To this end, a user may identify one or more media items 136 associated with a range of beats per minute by selecting one of the additional beats per minute taxonomy concepts 312. For instance, a user may select the beats per minute taxonomy concept 312 entitled "Blues-Like BMP" to search media items 136 having a range of beats per minute commonly associated with media items 136 within the "Blues" music genre.

In other embodiments, user interface 179a may include other beats per minute taxonomy concepts defined by one or more user friendly descriptive terms, such as, for example, "Very Slow Music", "Slow Music", "Fast Music", and so forth, where each of the beats per minute taxonomy concepts is associated with a range of beats per minute. To this end, a user may identify one or more media items 136 associated with a range of beats per minute by selecting one of the beats per minute taxonomy concepts.

For instance, the beats per minute taxonomy concept entitled "Very Slow Music" may be associated with a range of beats per minute, such as, for example, between 50 and 70. In this example, a user may select the beats per minute taxonomy concept 312 entitled "Blues-Like BMP" to search media items 136 having a range of beats per minute between 50 and 70.

In another embodiment, beats per minute taxonomy concepts 309 and/or additional beats per minute taxonomy concepts 312 may be used to search media items 136 or other items in other contexts. For example, such concepts may be employed to search for media items 136 to be rendered by a cloud player, media player, playlists associated with the user, and potentially other sources. To this end, a user may identify one or more media items 136 associated with various sources by selecting one of the beats per minute taxonomy concepts as described above. In addition, the beats per minute taxonomy concepts 309, 312 may be used for other contexts.

Figure 4:
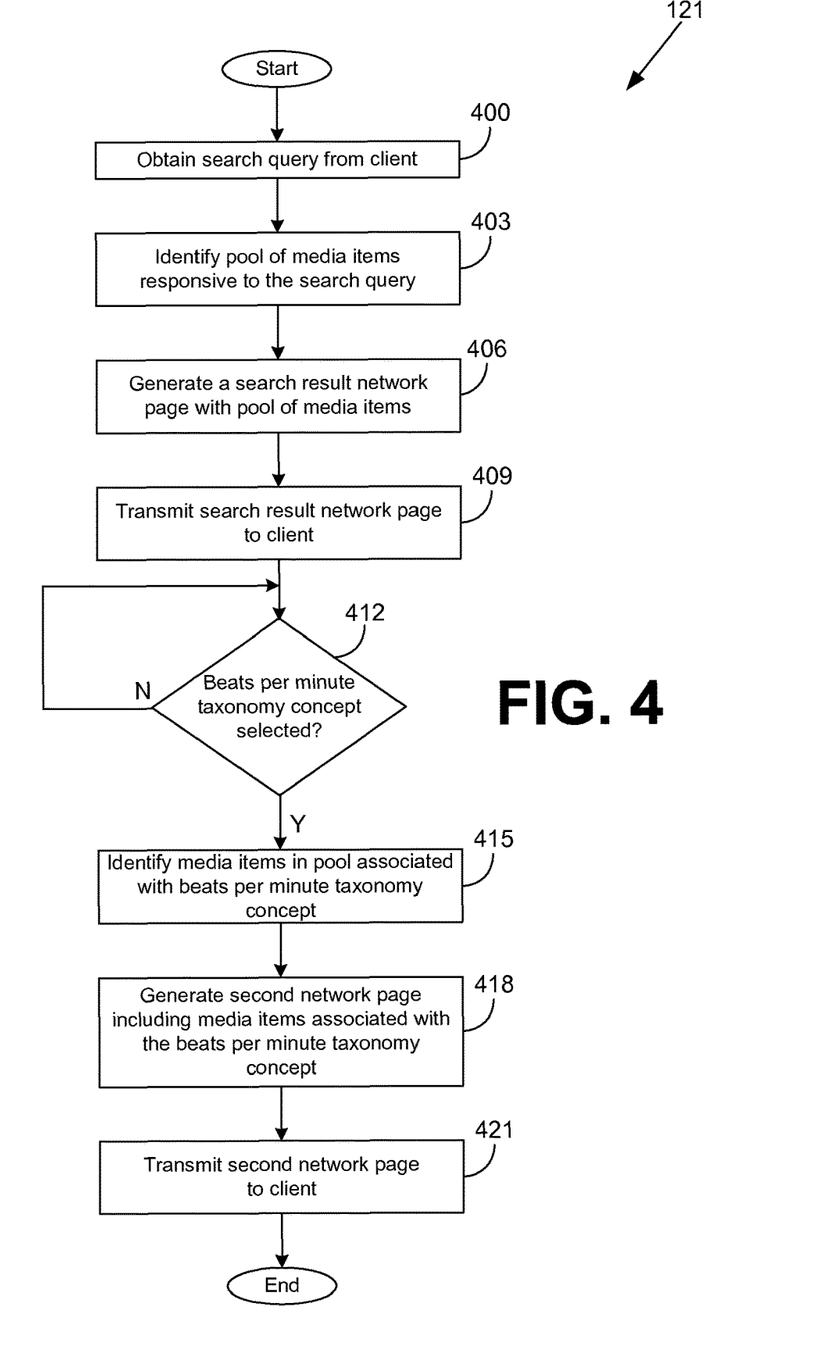
FIGS. 4-5 are flowcharts illustrating examples of functionality implemented as portions of a media search application executed in a computing device in the networked environment of FIG. 1 according to various embodiments of the present disclosure.

Turning now to FIG. 4, shown is a flowchart that provides one example of the operation of a portion of the media search application 121 according to various embodiments. It is understood that the flowchart of FIG. 4 provides merely an example of the many different types of functional arrangements that may be employed to implement the operation of the portion of the media search application 121 as described herein. As an alternative, the flowchart of FIG. 4 may be viewed as depicting an example of steps of a method implemented in the computing device 103 (FIG. 1) according to one or more embodiments.

To begin, a user may wish to search for media items 136 to purchase by inputting one or more search terms describing the media items 136, such as, a field to enter a beats per minute value, an artist name, a genre name, an album name, and potentially other data. To this end, beginning with box 400, the search application 121 obtains a search query from a client 106 (FIG. 1) over the network 109 (FIG. 1). For example, the search query may be entered in a text form within a browser 170 (FIG. 1) executing on the client 106 or by some other method. Thereafter, in box 403, the media search application 121 identifies a pool of media items 136 based at least in part on the search query. As described above, the pool of media items 136 may be selected based at least in part associations between the search terms entered by the user and the media item metadata 143 associated with each of the media items 136. Then, in box 406, the media search application 121 generates one or more search result network pages including the pool of media items 136. Lastly, in box 409, the media search application 121 encodes the search result network pages for rendering by the browser 170 and sends the search result network pages to the client 106 by way of the network 109.

As noted above, the generated search result network page includes one or more beats per minute taxonomy concepts associated with the pool of media items 136. To this end, in box 412, the media search application 121 waits for the user to select one of the beats per minute taxonomy concepts. If the user does not select any of the beats per minute taxonomy concepts, then the search application 121 ends. Alternatively, if a user selects one of the beats per minute taxonomy concepts, then, in box 415, the media search application 121 identifies a portion of the pool of media items 136 associated with the selected beats per minute taxonomy concepts. Thereafter, in box 418, the media item each application 121 generates one or more second network pages including the portion of the pool of media items 136 associated with the selected beats per minute taxonomy concepts. Lastly, in box 421, the media search application 121 transmits the one or more second network pages to the client 106.

Figure 5:
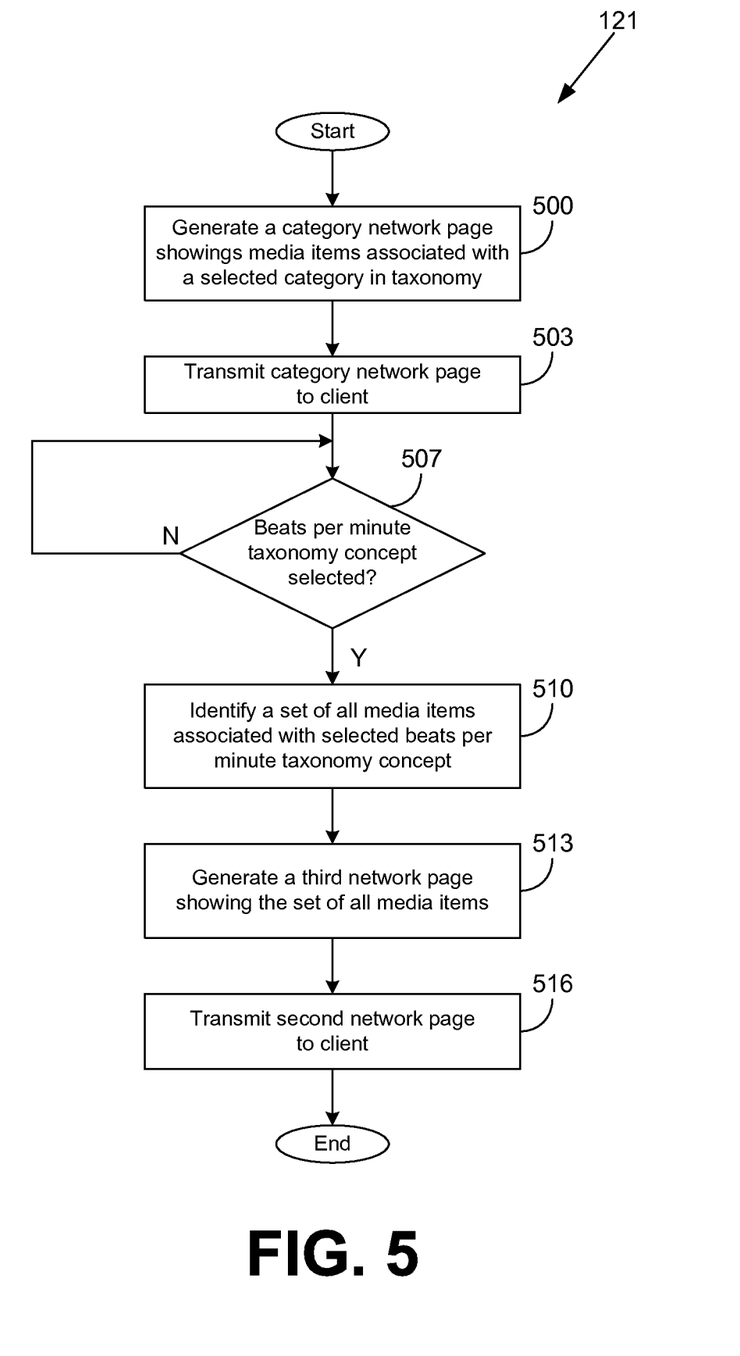

Turning now to FIG. 5, shown is a flowchart that provides another example of the operation of a portion of the media search application 121 according to various embodiments. It is understood that the flowchart of FIG. 5 provides merely an example of the many different types of functional arrangements that may be employed to implement the operation of the portion of the media search application 121 as described herein. As an alternative, the flowchart of FIG. 5 may be viewed as depicting an example of steps of a method implemented in the computing device 103 (FIG. 1) according to one or more embodiments.

As described above, in some cases a user may wish to search media items 136 by selecting one or more categories within a taxonomy. In this case, beginning with box 500, the media search application 121 generates one or more category network pages showing one or more media items 136 associated with the selected category taxonomy. Then, in box 503, the media search application 121 transmits the category network pages to the client 106. Thereafter, in box 507, the search application 121 waits for the user to select one of the beats per minute taxonomy concepts corresponding to the media items 136 associated with the selected category. If the user does not select any of the beats per minute taxonomy concepts, then the media search application 121 may end. However, if the user selects one of the beats per minute taxonomy concepts, then in box 510, the media search application 121 identifies a set of the media items 136 associated with the selected beats per minute taxonomy concept. Thereafter, in box 513, the media search application 121 generates one or more network pages including the set of media item 136 associated with the selected beats per minute taxonomy concepts. Lastly, in box 516, the media search application 121 transmits the one or more network pages to the client 106.

Figure 6:
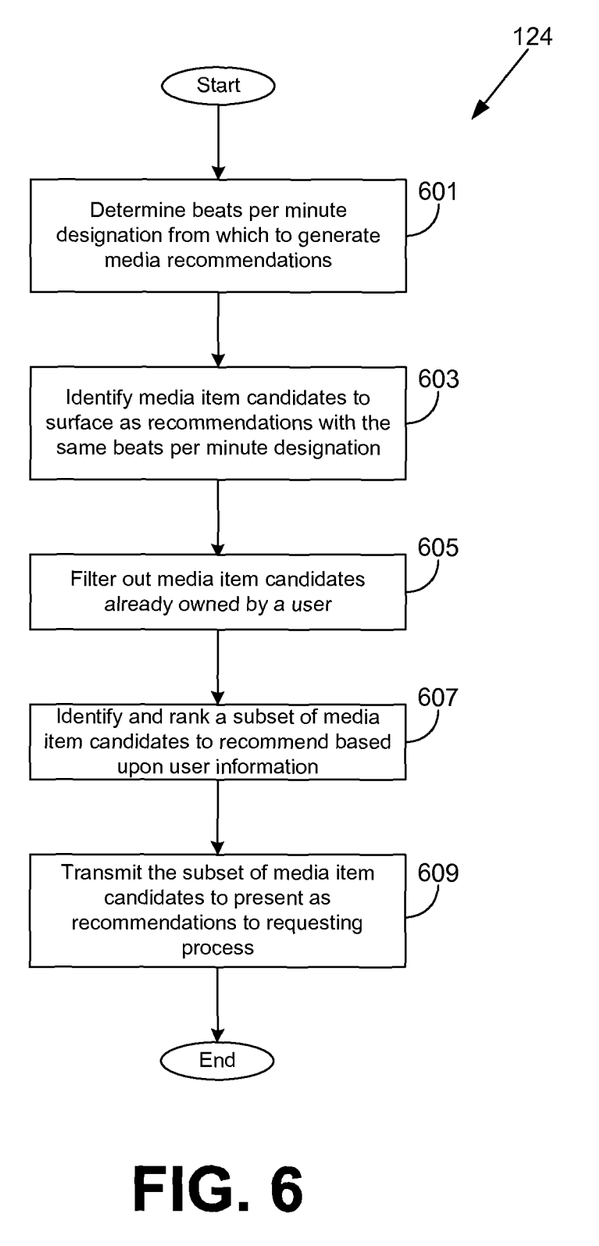
FIG. 6 is a flowchart illustrating one example of functionality implemented as portions of a media recommendation application executed in a computing device in the networked environment of FIG. 1 according to various embodiments of the present disclosure.

Turning now to FIG. 6, shown is a flowchart that provides one example of the operation of a portion of the media recommendation application 124 according to various embodiments. It is understood that the flowchart of FIG. 6 provides merely an example of the many different types of functional arrangements that may be employed to implement the operation of the portion of the media recommendation application 124 as described herein. As an alternative, the flowchart of FIG. 6 may be viewed as depicting an example of steps of a method implemented in the computing device 103 (FIG. 1) according to one or more embodiments.

The media recommendation application 124 may execute a search of the media items 136 to identify one or more media candidates based upon a beats per minute value. To this end, beginning with box 601, the media recommendation application 124 determines a beats per minute designation from which to generate media item recommendations. As described above, the beats per minute may be determined from a reading of an input device, such as, a pedometer or a heart rate monitor. Alternatively, the beats per minute value may be determined from a media item the user is listening to, the purchase or browse history associated with the user account 150, as well as a variety of other information associated with the user. Alternatively, other approaches may be employed as described above.

Upon determining the beats per minute value, in box 603, the media recommendation application 124 identifies media item candidates to surface as recommendations with the same beats per minute value or that fall within a beats per minute designation. Then, in box 605, the recommendations application filters the media items 136 from the media item candidates that are already possessed by the user. Thereafter, in box 607, the media recommendation application 124 identifies a subset of media item candidates to send to the user as recommendations based at least upon user information. Lastly, in box 609, the media recommendation application transmits the subset of media item candidates to requesting process.

In one embodiment, the media recommendation application 124 may rank the media items 136 in the subset of media item candidates identified in step 607 the user is most likely to purchase based upon user information. In one embodiment, the media recommendation application 124 may identify the top, for example, three media items 136 with the highest ranking to send to the user as recommendations.

Figure 7:
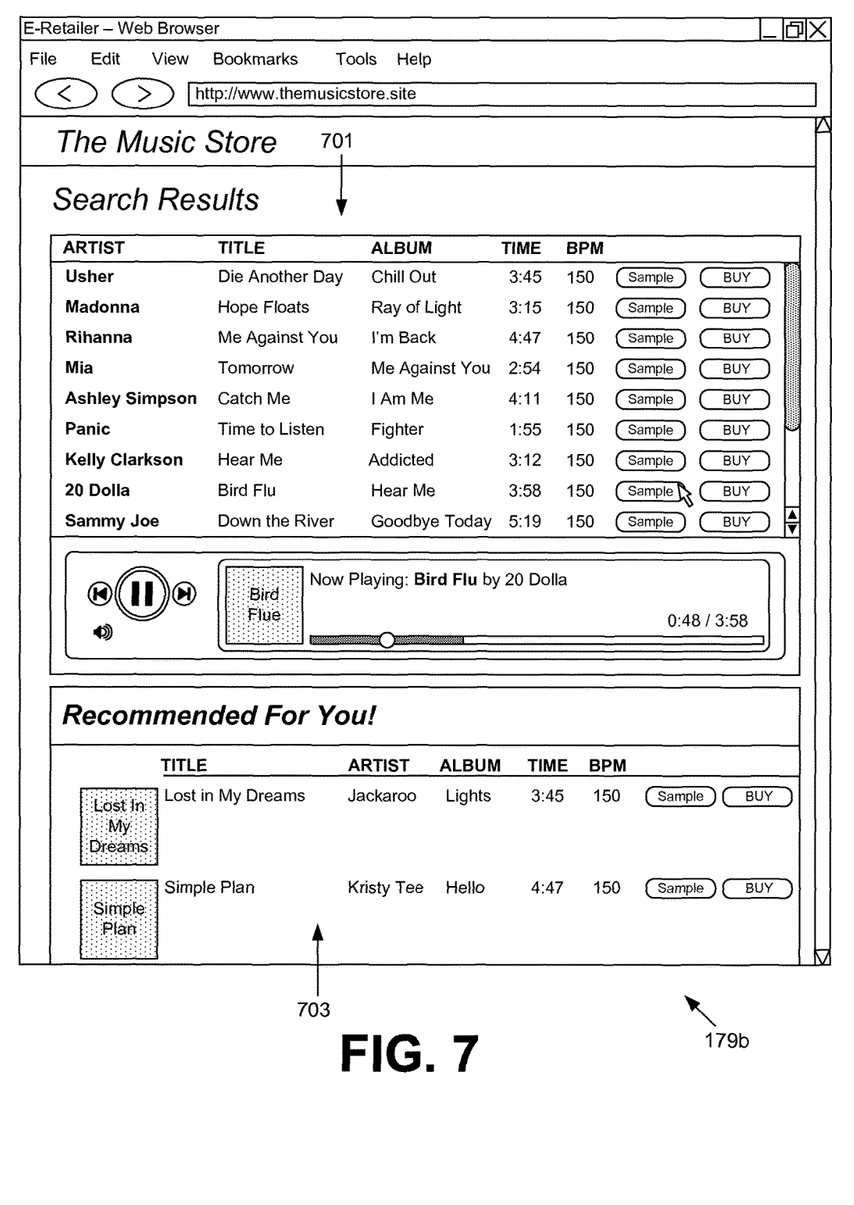
FIG. 7 is a drawing of an example of a user interface rendered by a client in the networked environment of FIG. 1 according to various embodiments of the present disclosure.

Referring next to FIG. 7, shown is a non-limiting example of a user interface 179 (FIG. 1), denoted herein as user interface 179*b* rendered by a browser 170 (FIG. 1) executed on a client 106 (FIG. 1) according to various embodiments of the present disclosure.

As a non-limiting example, in FIG. 7, user interface 179*b* shows a pool of media items 701 identified by the media search application 121. Additionally, user interface 179*b* comprises media item recommendations 703 identified by the media recommendation application 124 as described above.

Figure 8:
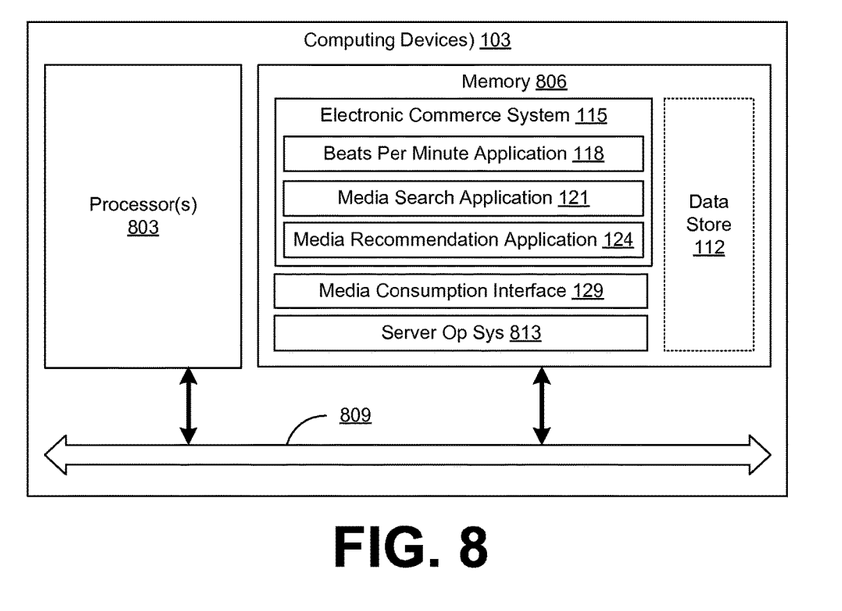
FIG. 8 is a schematic block diagram that provides one example illustration of a computing device employed in the networked environment of FIG. 1 according to various embodiments of the present disclosure.

With reference to FIG. 8, shown is a schematic block diagram of the computing device 103 according to an embodiment of the present disclosure. The computing device 103 includes a processor circuit, for example, having a processor 803 and a memory 806, both of which are coupled to a local interface 809. To this end, the computing device 103 may comprise, for example, at least one server computer or like device. The local interface 809 may comprise, for example, a data bus with an accompanying address/control bus or other bus structure as can be appreciated.

Stored in the memory 806 are both data and several components that are executable by the processor 803. In particular, stored in the memory 806 and executable by the processor 803 are beats per minute application 118, the search application 121, the recommendation application 124, media consumption interface 129, server op system 813, and potentially other applications. Also stored in the memory 806 may be a data store 112 and other data. In addition, an operating system may be stored in the memory 806 and executable by the processor 803.

It is understood that there may be other applications that are stored in the memory 806 and are executable by the processors 803 as can be appreciated. Where any component discussed herein is implemented in the form of software, any one of a number of programming languages may be employed such as, for example, C, C++, C#, Objective C, Java, JavaScript, Perl, PHP, Visual Basic, Python, Ruby, Delphi, Flash, or other programming languages.

A number of software components are stored in the memory 806 and are executable by the processor 803. In this respect, the term "executable" means a program file that is in a form that can ultimately be run by the processor 803. Examples of executable programs may be, for example, a compiled program that can be translated into machine code in a format that can be loaded into a random access portion of the memory 806 and run by the processor 803, source code that may be expressed in proper format such as object code that is capable of being loaded into a random access portion of the memory 806 and executed by the processor 803, or source code that may be interpreted by another executable program to generate instructions in a random access portion of the memory 806 to be executed by the processor 803, etc. An executable program may be stored in any portion or component of the memory 806 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 806 is defined herein as including both volatile and nonvolatile memory and data storage components. Volatile components are those that do not retain data values upon loss of power. Nonvolatile components are those that retain data upon a loss of power. Thus, the memory 806 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 803 may represent multiple processors 803 and the memory 806 may represent multiple memories 806 that operate in parallel processing circuits, respectively. In such a case, the local interface 809 may be an appropriate network 109 (FIG. 1) that facilitates communication between any two of the multiple processors 803, between any processor 803 and any of the memories 806, or between any two of the memories 806, etc. The local interface 809 may comprise additional systems designed to coordinate this communication, including, for example, performing load balancing. The processor 803 may be of electrical or of some other available construction.

Although the beats per minute application 118, the media search application 121 and the media recommendation application 124, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

The flowcharts of FIGS. 2 and 4-6 show the functionality and operation of an implementation of portions of the beats per minute application 118, the media search application 121 and the media recommendations application 124. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 803 in a computer system or other system. The machine code may be converted from the source code, etc. If embodied in hardware, each block may represent a circuit or a number of interconnected circuits to implement the specified logical function(s).

Although the flowcharts of FIGS. 2 and 4-6 show a specific order of execution, it is understood that the order of execution may differ from that which is depicted. For example, the order of execution of two or more blocks may be scrambled relative to the order shown. Also, two or more blocks shown in succession in FIGS. 2 and 4-6 may be executed concurrently or with partial concurrence. Further, in some embodiments, one or more of the blocks shown in FIGS. 2 and 4-6 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the beats per minute application 118, the media search application 121 and the media recommendations application 124, that comprises software or code can be embodied in any non-transitory computer-readable medium for use by or in connection with an instruction execution system such as, for example, a processor 803 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A system, comprising:
    at least one computing device;
    a media search application executable in the at least one computing device; and
    a media recommendation application executable in the at least one computing device,
    wherein the media search application is configured to cause the at least one computing device to at least:
        execute a search query for a pool of media items, the search query comprising at least one search term;
        obtain the pool of media items based on the at least one search term of the search query;
        generate a user interface having a first region comprising a display of the pool of media items; a second region comprising a plurality of selectable links of taxonomy concepts that correspond to the pool of media items; and a third region comprising one or more media item recommendations for a user associated with a user account; and
        send the user interface to the user associated with the user account,
    wherein the media recommendation application is further configured to cause the at least one computing device to at least:
        determine a beats per minute value for generating at least one media item recommendation from a playlist associated with the user account, wherein the playlist identifies a first plurality of media items and the beats per minute value is calculated from one or more of the first plurality of media items identified in the playlist;
        identify a second plurality of media items within the pool of media items having a respective one of a plurality of beats per minute taxonomy concepts associated with the beats per minute value; and
        tailor the searching of media items for the user by communicating the at least one media item recommendation to the user within the third region of the user interface, wherein the at least one media item recommendation indicates at least one of the second plurality of media items,
    wherein the plurality of beats per minute taxonomy concepts is a first plurality of beats per minute taxonomy concepts, and the media recommendation application is further configured to cause the at least one computing device to determine, for at least one of the first plurality of media items, at least one of a second plurality of beats per minute taxonomy concepts.

2. The system of claim 1, wherein the at least one of the second plurality of beats per minute taxonomy concepts is determined by obtaining, for at least one of the first plurality of media items, at least one of the second plurality of beats per minute taxonomy concepts from a data store.

3. The system of claim 2, wherein the media recommendation application is further configured to cause the at least one computing device to store the at least one of the second plurality of beats per minute taxonomy concepts in a data store in association with the at least one of the first plurality of media items.

4. The system of claim 3, wherein the respective one of the plurality of beats per minute taxonomy concepts is within a predefined delta of the beats per minute value.

5. The system of claim 4, wherein the predefined delta comprises a predefined percentage of the beats per minute value.

6. The system of claim 5, wherein the beats per minute taxonomy concept is a description, and the media recommendation application is further configured to cause the at least one computing device to identify the second plurality of media items as having the respective one of the plurality of beats per minute taxonomy concepts matching the description.

7. The system of claim 6, wherein the beats per minute value is based at least in part on a currently playing media item.

8. A method, comprising:
    executing, in a computing device, a search query for a pool of media items, the search query comprising at least one search term;
    obtaining, in the computing device, the pool of media items based on the at least one search term of the search query;
    generating, in the computing device, a user interface having a first region comprising a display of the pool of media items; a second region comprising a plurality of selectable links of taxonomy concepts that correspond to the pool of media items; and a third region comprising one or more media item recommendations for a user associated with a user account;
    sending, in the computing device, the user interface to a client device associated with the user account;
    determining, in the computing device, a beats per minute value for generating at least one media item recommendation from a playlist associated with the user account, wherein the playlist identifies a first plurality of media items and the beats per minute value is calculated from one or more of the first plurality of media items identified in the playlist;
    identifying, in the computing device, a second plurality of media items within the pool of media items having a respective one of a plurality of beats per minute taxonomy concepts associated with the beats per minute value, wherein the plurality of beats per minute taxonomy concepts is a first plurality of beats per minute taxonomy concepts;
    determining, for at least one of the first plurality of media items, at least one of a second plurality of beats per minute taxonomy concepts; and
    tailoring, in the computing device, the searching of media items for the user by at least filtering the second plurality of media items to exclude those of the second plurality of media items associated with the user account and communicating at least one media item recommendation for at least one of the second plurality of media items within the third region of the user interface.

9. The method of claim 8, wherein the second plurality of media items that are filtered and excluded are indicated in at least one of a purchase history of the user account or a media item collection of the user account.

10. The method of claim 8, wherein the beats per minute value comprises a descriptive term, and the second plurality of media items are identified as having the respective one of the plurality of beats per minute taxonomy concepts matching the descriptive term.

11. The method of claim 8, wherein the beats per minute value comprises a beats per minute range, and the second plurality of media items are identified as having the respective one of the plurality of beats per minute taxonomy concepts within the beats per minute range.

12. The method of claim 8, wherein the plurality of beats per minute taxonomy concepts comprises a plurality of beats per minute values, and further comprising calculating, in the computing device, at least one of the beats per minute values.

13. The method of claim 12, further comprising storing, in the computing device, the at least one of the beats per minute values in a data store in association with a respective one of the second plurality of media items.

14. A non-transitory computer-readable medium embodying a program executable in a computing device, the program, when executed by a processor of the computing device, causing the computing device to at least:

execute a search query for a pool of media items, the search query comprising at least one search term;

obtain the pool of media items based on the at least one search term of the search query;

generate a user interface having a first region comprising a display of the pool of media items; a second region comprising a plurality of selectable links of taxonomy concepts that correspond to the pool of media items; and a third region comprising one or more media item recommendations for a user associated with a user account;

send the user interface to a client device associated with the user account;

determine a beats per minute value for generating at least one media item recommendation from a playlist associated with the user account, wherein the playlist identifies a first plurality of media items and the beats per minute value is calculated from one or more of the first plurality of media items identified in the playlist;

identify a second plurality of media items within the pool of media items having a respective one of a plurality of beats per minute taxonomy concepts associated with the beats per minute value, wherein the plurality of beats per minute taxonomy concepts is a first plurality of beats per minute taxonomy concepts;

determine, for at least one of the first plurality of media items, at least one of a second plurality of beats per minute taxonomy concepts;

tailor the searching of media items for the user by at least filtering the second plurality of media items to exclude those of the second plurality of media items associated with the user account and communicating at least one media item recommendation for at least one of the second plurality of media items within the third region of the user interface.

15. The non-transitory computer readable medium of claim 14, wherein the second plurality of media items that are filtered and excluded are indicated in at least one of a purchase history of the user account or a media item collection of the user account.

16. The non-transitory computer readable medium of claim 14, wherein the beats per minute value comprises a descriptive term, and the second plurality of media items are identified as having the respective one of the plurality of beats per minute taxonomy concepts matching the descriptive term.

17. The non-transitory computer readable medium of claim 14, wherein the beats per minute value comprises a beats per minute range, and the second plurality of media items are identified as having the respective one of the plurality of beats per minute taxonomy concepts within the beats per minute range.

18. The non-transitory computer readable medium of claim 14, wherein the plurality of beats per minute taxonomy concepts comprises a plurality of beats per minute values, and further comprising calculating, in the computing device, at least one of the beats per minute values.

19. The non-transitory computer readable medium of claim 18, wherein the program further causes the computing device to store the at least one of the beats per minute values in a data store in association with a respective one of the second plurality of media items.

\* \* \* \* \*